United States Patent [19]

Kim et al.

[11] Patent Number: 5,004,737
[45] Date of Patent: Apr. 2, 1991

[54] QUATERNARY AMMONIUM-SUBSTITUTED STEROL DERIVATIVES

[75] Inventors: Young D. Kim; Byung J. Ha, both of Seoul, Rep. of Korea

[73] Assignee: Pacific Chemical Co., Ltd., Seoul, Rep. of Korea

[21] Appl. No.: 411,411

[22] Filed: Sep. 22, 1989

[51] Int. Cl.$^5$ .................. A61K 31/575; C07J 41/00
[52] U.S. Cl. .................. 514/182; 552/544; 552/546
[58] Field of Search ............ 552/544, 546; 514/182

[56] References Cited

U.S. PATENT DOCUMENTS 2,889,318  6/1959  Bergstrom .................. 552/544
3,013,009 12/1961  Marshall .................... 552/544

FOREIGN PATENT DOCUMENTS 4640510 11/1971 Japan.

OTHER PUBLICATIONS

Morrison and Boyd "Organic Chemistry", 3rd Ed., pp. 563–566, (1978).

Noguchi et al., CA:09950V (1972). (abstract for JP-4-6-40510).

Primary Examiner—Frederick E. Waddell
Assistant Examiner—Celia Chang
Attorney, Agent, or Firm—Millen, White & Zelano

[57] ABSTRACT

The present invention relates to a novel quaternary ammonium-substituted sterol derivative of the following formula:

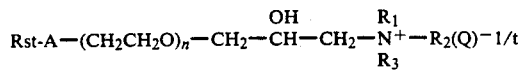

wherein Q represents an anion of a strong inorganic acid, A represents an oxygen, $R_1$, $R_2$, $R_3$, t, n, and the sterol Rst are defined as herein. The compounds of the present invention as a result of introducing a cationic group into hydroxy group of sterols of ethoxylated compounds thereof which are non-ionic, shows the enhanced substantivity against substrate having, on its surface, an anionic characters under normal conditions such as skin and hair of human being. The compound of the present invention can be used in the field of cosmetics.

6 Claims, No Drawings

QUATERNARY AMMONIUM-SUBSTITUTED STEROL DERIVATIVES

FIELD OF THE INVENTION

The present invention relates to quaternary ammonium-substituted sterol derivatives. Specifically, the present invention relates to compounds having quaternary ammonium groups in sterols, stanols or ethoxylated sterols.

SUMMARY OF THE INVENTION

The present invention relates to novel quaternary ammonium-substituted sterol derivatives of the following general formula (I) produced by processes comprising reacting sterols, stanols or ethoxylated sterols with quaternary ammonium epoxide salts of the following general formula (II) or quaternary ammonium amine salts of the following general formula (III):

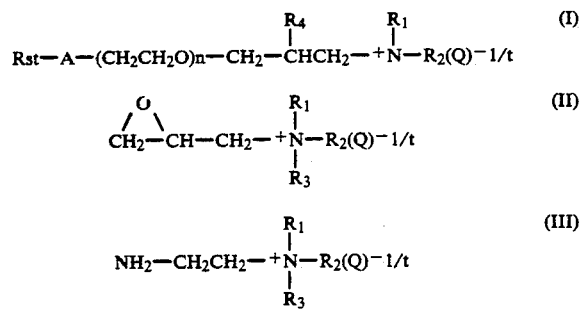

wherein, Q represents anion of a strong inorganic acid which includes Cl, Br and I; $R_1$, $R_2$ and $R_3$ represent, same or different, an alkyl group having up to 18 carbon atoms or an olefin group; t is the valence of Q; A represents oxygen atom or NH; n is the integer of 0 to 50; $R_4$ represents H or OH; and Rst represents the skeletal structure of sterols or the structure of stanols which are formed by reduction of the double bond between the carbon atoms 5 and 6 at the skeletal structure of sterols.

DESCRIPTION OF THE RELEVANT PRIOR ART

Sterols are a component of lipids and have an important role of constituting tissues [See: Albert L. Lehninger, "Principles of Biochemistry", Worth Publishers, Inc., p304 (1982)]. Recently, it has been reported that the two major components, cholesterol and desmosterol (cholesta -5, 24-dien-3β-ol), which is the precursor of the cholesterol, were found in the sterol fractions obtained from internal lipids of wool fat [See: Douglas J. Gale, Raymond I. Logen, and Donald E. Rivett, Textile Research Journal, p539-542, (Sept. 1987)].

Sterols are a nature material which present in a living body and exhibit several activities of biologically important. It is known that sterols provide good effects such as stability or elasticity to the skin or the hair in case of using as an additive in the external agents. Moreover, parts of them are already commercially available and used as sterols as such or as a modified structure whose water solubility is increased by ethoxyfying the hydroxy group of sterols [For example: Generol 122, Generol 122 E-25, Generol 122E-16, Generol 122E-5; manufactured by Henkel AG].

The fact is already well known that the cationic surfactant shows strong substantivity to the substrate having negative charge under normal condition, for example skin or hair of the human being [See: "Surfactants, in Cosmetics", Vol. 16, Marcel Dekker, 1985, p285-287]. There are a number of examples using the quaternary ammonium compound in the preparation of haircare products such as conditioning shampoo, etc., and their effects have been proved in numerous literatures [See: XIVth IFSCC Congress, Barcelona, 1986, Vol. I, p335-369; Edward J. Murphy, Soap/Cosmetics/Chemical Specialities, p38-40, Feb. 1980; Anthony M. Schwartz and James W. Perry "Surface Active Agents", Interscience Publishers, Inc., New York, 151-200, 1949].

Almost all of the commercially available quaternary ammonium salts are based on the property derived from the positively-charged quaternary nitrogen atom, which makes the quaternary cation to be adsorbed to the negatively-charged surface, for example skin, hair and the likes. The adsorption or the substantivity of the quaternary ammonium salts is increased as their water-solubility becomes lower and as the molecular weight of cationic hydrophobe becomes larger [See: K. Ohbu, T. Tamura, N. Mizushima and M. Fukuda, Colloid & Polymer Sci. 264, p798-802 (1986)].

DETAILED DESCRIPTION OF THE INVENTION

The novel quaternary ammonium-substituted sterol derivatives according to the present invention are cationic surfactants which are produced by introducing a quaternary ammonium group into the aforementioned sterols, stanols or compounds obtained by ethoxylating the sterols, and have strong substantivity to the polypeptide substrate such as skin or hair.

Most of the conventional quaternary ammonium salts were alkyl quaternary, dialkyl quaternary, etc. In contrast, the compounds of the present invention are produced by introducing a quaternary ammonium group into sterols or sterol derivatives which are nature materials and known to have excellent safety to the skin. As a result, in comparison with the alkyl quaternary or the dialkyl quaternary, the compounds of the present invention show significant safety to the skin. Recently, it has been reported that quaternary ammonium derivatives of cholesterols were produced to be used in the synthesis of polymerizable and nonpolymerizable liquid-crystalline [See: S. K. Abid and D. C. Sherrington, Polymer Communications, 1987, Vol. 2, January, p16-19; Iwhan Cho and Kwang-Choon Chung, Macromolecules, 1984, 17, p2935-2937]. However, unlike the compounds of the present invention, the above-mentioned quaternary ammonium derivatives of cholesterols have a quaternary ammonium group bonded via ester linkage, and this is apparently different from the bonding form of the compounds of this invention.

Sterols used in the preparation of the quaternary ammonium substituted derivatives of this invention include, for example, cholesterols and lanosterols found in animal cell membrane and other various sterols found in plant cell membrane.

The cholesterols found in animal cell membrane are contained abundantly in the protoplasmic membrane of eucaryotic cells such as red blood cells, liver cells and neurocytes surrounded by cytoplasm but do not present in procaryotes.

In view of the structure, the cholesterols are characterized by having an alcoholic hydroxy group at C-3.

Cholesterols, together with phospholipids, consist of the cell membrane and are also responsible to the constitution of the myelin sheath of nerve tissue.

Lanosterols are contained abundantly in non-saponificated part of the wool fat and represented by the following structural formula (IV):

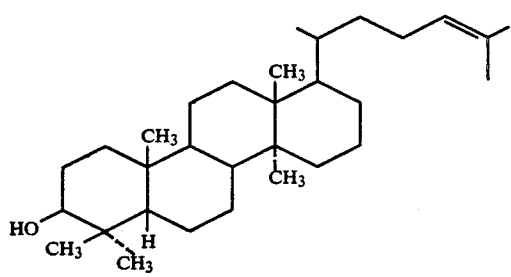

The sterols found in plant cell membrane include, for example, stigmasterol, sitosterol, campesterol, etc. and their structures are as follows:

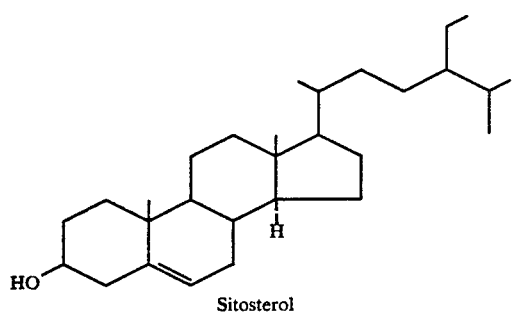
Sitosterol (V)

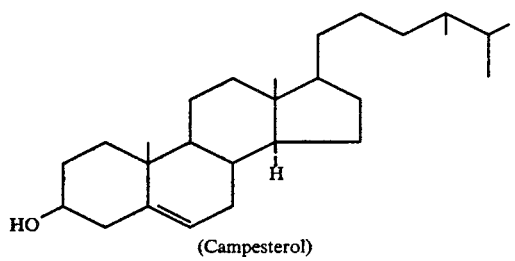
(Campesterol)

(VI)

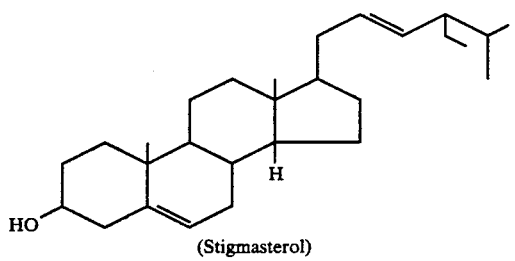
(Stigmasterol)

(VII)

Phytosterols, what are called, present in every higher plant cells and almost all of them are sterols.

The major difference among the above three sterols is found in the side chain attached to C-17 carbon of the sterol skeleton. The cholesterol molecules have —OH group at C-3, which constitutes the partial group of the polar head. Other parts of the molecules have a relatively fixed nonpolar structure. Four rings of them are very rigid and, therefore, the mobility of the membrane is lowered by the presence of cholesterols. Hydroxy group constitutes the polar part and other parts of the molecule are hydrophobic.

There are two kinds of forms, i.e. alpha-form and beta-form in the structure of cholesterol and the major structural difference between them is as follows:

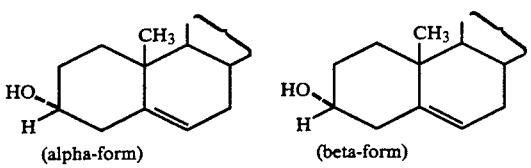
(alpha-form)   (beta-form)

Between the above two kinds of forms, the beta-form is known to present dominantly in nature. Accordingly, cholesterols, in general, designate their beta-form. And also, the double bond of the cholesterols can be reduced to obtain the two kinds of isomers. Between the two isomers, S-alpha-Cholestan-3-ol of the following structure is predominant:

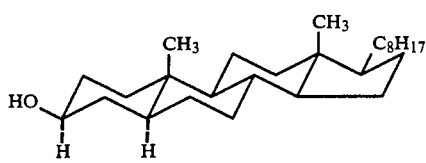

The objective compound of the general formula (I) according to the present invention can be produced by the following methods.

Method A

The compound of the general formula (I) can be produced by reacting the compound of the following structural formula (X) or (XI) with the quaternary ammonium epoxide salt of the general formula (II) in the presence of sodium hydroxide; or

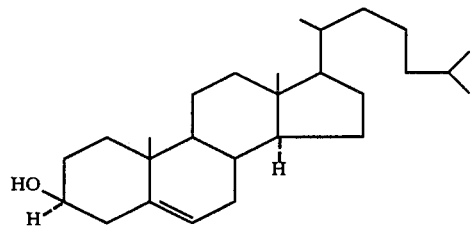

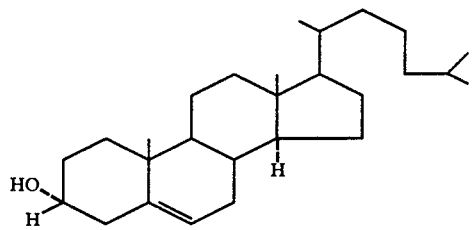

reacting the compound of the following structural formula (XII) or (XIII) produced by the reduction of the corresponding compound (X) or (XI) using hydrogen in the presence of platinum catalysts with the quaternary ammonium epoxide salt of the general formula (II) in the presence of sodium hydroxide; or

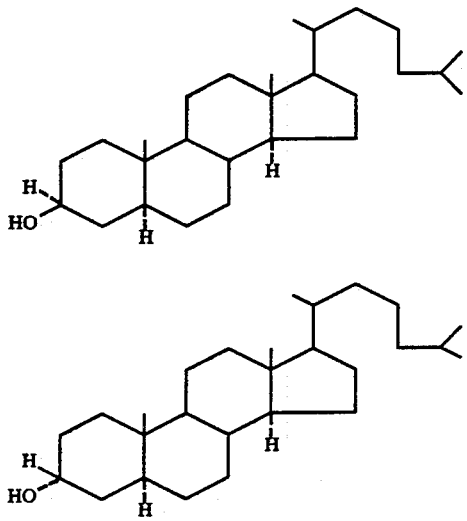

reacting the compound of the structural formula (V), (VI) or (VII) of which the hydroxy groups are epoxified by the number of n (n is the integer of 5 to 25) (Trademark: Generol 122E-5, Generol 122E-16, Generol 122E-25, etc. manufactured by Henkel AG) with the quaternary ammonium epoxide salt of the general formula (II) in the presence of sodium hydroxide to form the ether linkage and, if necessary, carrying out gel chromatography to remove unreacted materials.

Method B

The compound of the general formula (I) can be produced by reacting the compound of the structural formula (X) or (XI) of which the hydroxy group is replaced with an appropriate leaving group such as tosyl group with the quaternary ammonium amine salt of the general formula (III); or reacting the compound of the formula (XII) or (XIII) obtained by the reduction of the corresponding compound (X) or (XI) using hydrogen in the presence of platinum catalysts, after replacing its hydroxy group with an appropriate leaving group, with the quaternary ammonium amine salt of the general formula (III).

The quaternary ammonium epoxide of the general formula (II) used as an reactant in the present invention can be produced by the following reaction scheme:

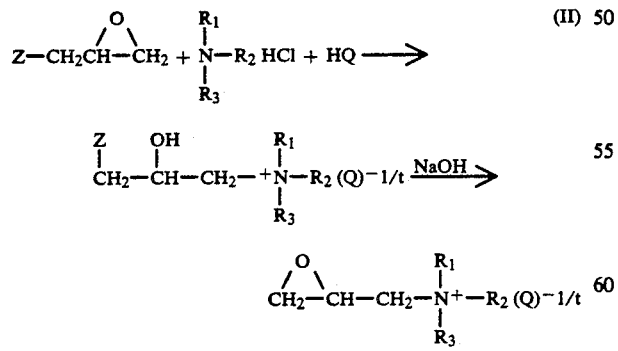

wherein, Q and t are as defined above, and Z represents Cl, Br or I.

The tertiary amine salt used in the reaction can be suitably selected from the group consisting of trimethylamine hydrochloride, triethylamine hydrochloride, dimethylbenzylamine hydrochloride, dimethylcyclohexylamine hydrochloride and the like.

Among the reactants used in the present invention, the compound of the general formula (III), wherein $R_1$, $R_2$ and $R_3$ are methyl groups, respectively, and Q is chloride, is well known and can be produced by the method described in J. Med. Chem., 8, 650 (1965), i.e. by reacting N,N-dimethylenediamine of the following structural formula (XV), after protecting its primary amine with an acetyl, with methyl iodide ($CH_3I$) to afford the quaternary ammonium salt and then replacing the anion $I^-$ with $Cl^-$. Finally, the acetyl group is hydrolyzed with strong hydrochloric acid and followed by the neutralization to produce the compound of the following structural formula (III) wherein $R_1$, $R_2$ and $R_3$ are methyl groups, respectively, and Q is chloride.

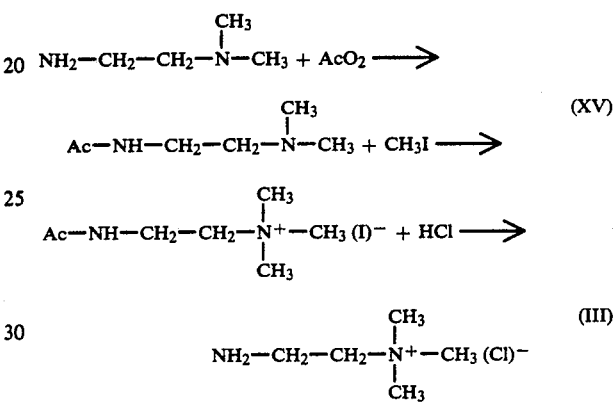

The compound of the present invention can be used in shampoo, hair rinse, hair treatment, cream, lotion, compact, foundation. Especially, it is effective in providing the hair cosmetics such as shampoo, hair rinse and hair treatment with the conditioning effects.

The formulation examples of the present invention will be described hereinafter.

FORMULATION EXAMPLE 1: SHAMPOO

| | |
|---|---|
| 1. quaternary ammonium-substituted sterol derivative | 0.5 g |
| 2. sodium laurylsulfate (30%) | 40.0 g |
| 3. cocoamphocarboxypropionate (70%) | 10.0 g |
| 4. laurylmyristoyl D.E.A. | 5.0 g |
| 5. propylene glycol | q.s. |
| 6. preservative | q.s. |
| 7. citric acid | q.s. |
| 8. colorant | q.s. |
| 9. perfume | q.s. |
| 10. purified water | to 100.0 g |

The components 1 to 6 and 10 were mixed and the mixture thus obtained was heated at 70° C. with stirring. To this, the components 7 to 9 were added with stirring and cooled to afford the objective product.

FORMULATION EXAMPLE 2: HAIR RINSE

| | |
|---|---|
| 1. quaternary ammonium-substituted sterol derivative | 0.5 g |
| 2. stearalkonium chloride | 0.8 g |
| 3. stearyl alcohol | 0.5 g |
| 4. cetyl alcohol | 0.5 g |
| 5. polyoxyethylene(2) cetylether | 1.0 |
| 6. propylene gylcol | 5.0 g |
| 7. preservative | q.s. |

-continued

| | |
|---|---|
| 8. colorant | q.s. |
| 9. perfume | q.s. |
| 10. purified water | to 100.0 g |

The compounds 2 to 6 were mixed and the mixture thus obtained was heated at 65° C. while stirring. After adding the components 1 to 7, the resulting mixture was emulsified and cooled to 30° C. to afford the objective product.

FORMULATION EXAMPLE 3: SKIN LOTION

| | |
|---|---|
| 1. quaternary ammonium-substituted sterol derivative | 0.5 g |
| 2. ethanol | 15.0 g |
| 3. L serine | 0.5 g |
| 4. propylene glycol | 1.0 g |
| 5. polyoxyethylene oleylether | 1.5 g |
| 6. preservative | q.s. |
| 7. colorant | q.s. |
| 8. perfume | q.s. |
| 9. purified water | to 100.0 g |

The components 1 to 9 were mixed at room temperature and followed by stirring and filtering to afford the objective product.

The present invention will be described more specifically; by way of examples which show the methods for producing the quaternary ammonium-sustituted sterol derivatives of this invention.

EXAMPLE 1

To 20-30 ml of isopropyl alcohol was added 10 g (0.026 mol) of cholesterols and, while stirring, 0.2 ml of NaOH 10% was poured thereinto. After raising the temperature to 30° C., 8.44 g (0.039 mol) of the solution of 2,3-epoxypropyltrimethylammonium chloride (70% aqueous solution) was added slowly by drops.

When the addition was finished, the resulting mixture was maintained at 50°-55° C. for 5 hours and, after neutralization with 0.156 ml of acetic acid, maintained again for 30 minutes. Thereafter, the crystals were precipitated by the addition of excess amounts of isopropyl alcohol. By the filtering, the filterate was removed and the precipitates were dried in a vacuum desiccator at 40°-50° C. for 8 hours to give 12.6 g of quaternary ammonium-substituted cholesterol.

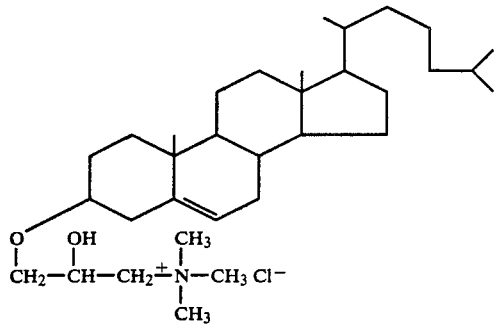

EXAMPLE 2

(A) Into a conical flask was charged 40 ml of freshdistilled pyridine and, after cooling in a cooling bath containing ice and salts, 7.45 g (0.033 mol) of toluene-p-sulfonyl chloride was added slowly and the mixture was maintained for 30 minutes, then the color of the solution was change into yellow. To this was added 11.5 g (0.033 mol) of cholesterols slowly with stirring and the reaction mixture was charged into a stopped flask. After keeping at room temperature for 5 days, 75 g of cooled distilled water was added, and, then, sticky and syrupy substance was began to form.

The supernatant was removed by the decantation, and the syrupy substance was completely dissolved by the addition of 25 ml of methylene chloride. The solution was washed with 2M of cooled hydrochloric acid twice or three times and then with distilled water, saturated sodiumbicarbonate solution and distilled water sequentially. The methylne chloride layer was seperated and dried sufficiently over magnesium sulfate. By the evaporation under reduced pressure methylene chloride was removed, and to the residue was added cold ether to give 12.2 g of cholesterols having tosyl group.

(B) Into a 250 ml two-neck round bottomed flask was charged 11.7 g (0.022 mol) of the reaction product obtained in the above Example 2. (A) dissolved completely in 150 ml of chloroform and cooled on a ice bath to 0° C. To this 3.23 g (0.024 mol) of 2-trimethylaminoethylammonium chloride dissolved completely in 40 g of methanol was added slowly by drops with stirring. After stirring at 0° C. for 24 hours, the methanol was removed and the solution of chloroform was washed with water to be neutralized. The small amount of water was removed over anhydrous magnesium sulfate and the solvent was evaporated under reduced pressure. By adding cold ethylether, the crystals were precipitated and dried in a desiccator to give 8.9 g of the quaternary ammonium-substituted cholesterol.

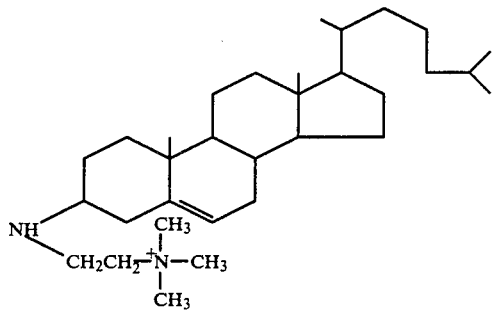

EXAMPLE 3

10 g (0.026 mol) of cholestanols was added to 20-30 ml of isopropanol and, after pouring thereinto 0.2 ml of 10% NaOH with stirring, the reaction was conducted in the same manner as in Example 1. When the reaction was completed, the reaction mixture was neutralized with acetic acid and the crystals were precipitated by the addition of excess amounts of isopropyl-alcohol. The crystals were filtered and dryed in a vacuum desiccator for 8 hours to give 13 g of the quaternary ammonium-substituted cholesterol.

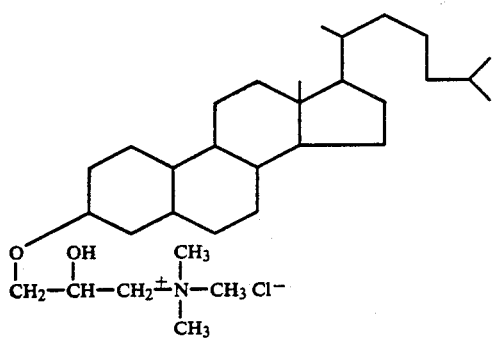

EXAMPLE 4

(A) Into a conical flask was charged 40 ml of fresh-distilled pyridine and, after cooling on a cooling bath containing ice and salts. 7.45 g (0.033 mol) of toluene-p-sulfonyl chloride was added slowly. After maintaining for 30 minutes, 11.66 g (0.03 mole) of cholestanols was added slowly with stirring and the reaction was conducted in the same manner as in Example 2. Yield: ca. 12.4 g (B) Into a 250 ml two-neck round bottomed flask was charged 11 g (0.02 mol) of reaction product obtained in the above Example 4. (A) dissolved completely in 150 ml of chloroform. After cooling to 0° C. on a cooling bath containing ice and salts, 2.77 g (0.02 mol) of 2-trimethylaminoethylammonium chloride dissolved completely in 40 ml of methanol was added slowly by drops with stirring, and the reaction was conducted in the same manner as in Example 2. (B) to give 8.35 g of quaternary ammonium-substituted cholestanols.

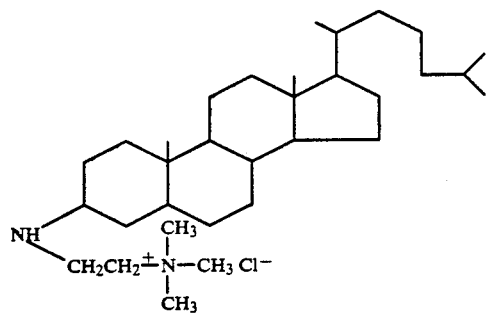

EXAMPLE 5

6 g of phytosterols obtained from soybean oil (Trademark: Generol 122, Henkel AG) was added to 35 ml of isopropyl alcohol, and to this the solution of 2,3-epoxy-propyldimethyldodecyl ammonium chloride (17.5 g) (68% aqueous solution) was added slowly. After raising the temperature to 40° C., about 0.6 ml of 45% sodium hydroxide was added slowly, and the reaction was conducted at 58° C. for 12 hours. When the reaction was completed, the solution was adjusted to pH 7.0 by the addition of 0.03M hydrochloric acid gradually and concentrated moderately using a vacuum rotary evaporator. To the residue was added excess amounts of isopropyl alcohol and stood to form the precipitates. The precipitates were filtered, evaporated again on a rotary evaporator and dissolved in minimum amounts of methanol. The purification was carried out by using gel chromatography with Sephadex LH-20 column using methanol as an eluent and the major fractions containing the purified product were collected and dried by the evaporation on a rotary evaporator to give about 6.9 g of the product.

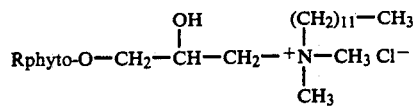

EXAMPLE 6

6 g of phytosterols obtained from soybean oil (Trademark: Generol 122, Henkel AG) was added to 40 ml of isopropyl alcohol and while stirring 22.4 g of the solution of 2,3-epoxypropyl dimethyloleyl ammonium chloride (67% aqueous solution) was added slowly. After raising the temperature to 45° C., 0.8 ml of 45% sodium bicarbonate solution was added slowly and the reaction was conducted at 55° C. for 15 hours. When the reaction was completed, the solution was adjusted to pH 6.8 with acetic acid and concentrated on a vacuum rotary evaporator. To the residue was added excess amounts of isopropyl alcohol and stood for 12 hours, then the precipiates were formed. By the filteration the precipitates were filtered and dried under vacuum condition. The purification was carried out in the same manner as in Example 5 to give ca. 7.1 g of the solid product.

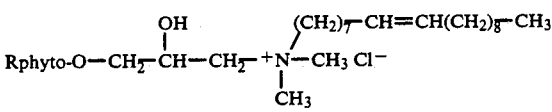

EXAMPLE 7

In a reaction vessel equipped with a separating funnel and a magnetic stirrer, 10 g of PEG-25 phytosterol was added to and dissolved in 80 ml of warm water at 40° C. While stirring slowly, 1.1M of 2,3-epoxypropyl trimethylammonium chloride and 1.1M of NaOH were added, and the reaction was conducted at 55° C. for 5 hours with continuously stirring. When the reaction was completed, the solution was adjusted to pH 6.8–7.0 by the addition of acetic acid.

The reaction mixture thus obtained was concentrated under reduced pressure, 11 ml of isopropyl alcohol was added thereinto and stood to form the precipitates. The precipitates were filtered off and the residue was dried under vacuum condition to obtain fale yellow solid mixture. For purification, the chromatography was carried out with Sephadex G-10 column using water as an eluent. Fractions containing the product were pooled and evaporated under vacuum condition to give ca. 9.2 g of product.

What is claimed is:

1. A quaternary ammonium-substituted sterol compound of the following formula (I):

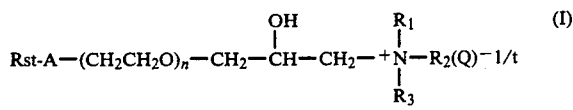

wherein Q represents an anion of a strong inorganic acid, $R_1$ represents alkyl or a monounsaturated alkenyl group having up to 18 carbon atoms; $R_2$ and $R_3$, the same or different from each other, are methyl or ethyl groups; t is the valence of Q; A represents an oxygen atom; n is an integer of 0 to 25; and $R_{st}$ represents a sterol selected from the group consisting of sitosterol, campesterol, stigmasterol, cholesterol, and lanosterol or a stanol obtained by the reduction of the double bond between carbon atoms 5 and 6 of said sterols.

2. A sterol compound of claim 1, wherein the stanol represents cholestanol.

3. The compound of claim 1, wherein Q is a halogen selected from the group consisting of chlorine, bromine, and iodine.

4. The compound of claim 1, wherein Q is chlorine.

5. The compound of claim 1, wherein Q is bromine.

6. The compound of claim 1, wherein Q is iodine.

* * * * *